(12) United States Patent  
Stokes et al.

(10) Patent No.: US 8,389,456 B2  
(45) Date of Patent: Mar. 5, 2013

(54) LOW INTERFACIAL TENSION SURFACTANTS FOR PETROLEUM APPLICATIONS

(75) Inventors: Kristoffer K. Stokes, Jamaica Plain, MA (US); Michael C. Berg, Somerville, MA (US); David Soane, Chestnut Hill, MA (US); Kevin T. Petersen, Cheshire, CT (US); John H. Dise, Somerville, MA (US); Atul C. Thakrar, Basking Ridge, NJ (US); Rosa Casado, Peabody, MA (US)

(73) Assignee: Soane Energy, LLC, Cambridge, MA (US)

( * ) Notice: Subject to any disclaimer, the term of this patent is extended or adjusted under 35 U.S.C. 154(b) by 255 days.

(21) Appl. No.: 12/635,241

(22) Filed: Dec. 10, 2009

(65) Prior Publication Data

US 2011/0065612 A1  Mar. 17, 2011

Related U.S. Application Data

(63) Continuation-in-part of application No. 12/481,072, filed on Jun. 9, 2009, now Pat. No. 8,227,383.

(60) Provisional application No. 61/060,004, filed on Jun. 9, 2008.

(51) Int. Cl.  
*C11D 3/20* (2006.01)  
*C11D 9/26* (2006.01)  
*C09K 8/60* (2006.01)

(52) U.S. Cl. ............. 510/188; 507/260; 507/261; 560/3  
(58) Field of Classification Search .................. 510/188; 507/260, 261; 560/3  
See application file for complete search history.

(56) References Cited

U.S. PATENT DOCUMENTS

| | | | |
|---|---|---|---|
| 3,381,022 A | 4/1968 | Le Suer | |
| 3,522,179 A | 7/1970 | Le Suer | |
| 3,542,680 A | 11/1970 | Le Suer | |
| 4,089,803 A | 5/1978 | Bessler | |
| 4,125,382 A | 11/1978 | O'Brien | |
| 4,219,431 A | 8/1980 | Chibnik | |
| 4,240,970 A * | 12/1980 | Chibnik | 549/233 |
| 4,266,610 A | 5/1981 | Meister | |
| 4,300,634 A | 11/1981 | Clampitt | |
| 4,396,530 A | 8/1983 | Duke | |
| 5,268,112 A | 12/1993 | Hutchins et al. | |
| 5,292,843 A | 3/1994 | Jenkins et al. | |
| 7,534,829 B2 | 5/2009 | Tai et al. | |
| 7,572,757 B1 * | 8/2009 | Gupta et al. | 507/262 |
| 2003/0222026 A1 | 12/2003 | Carey et al. | |
| 2003/0224963 A1 | 12/2003 | Scheibel | |
| 2009/0305933 A1 | 12/2009 | Stokes et al. | |

FOREIGN PATENT DOCUMENTS

| WO | 2006131541 A1 | 12/2006 |
|---|---|---|
| WO | 2008033709 A2 | 3/2008 |

* cited by examiner

*Primary Examiner* — Brian P Mruk  
(74) *Attorney, Agent, or Firm* — Elmore Patent Law Group, P.C.; Mahreen Chaudhry Hoda; Carolyn S. Elmore, Esq.

(57) ABSTRACT

The invention relates to a class of novel surfactants that have utility in the recovery and/or extraction of oil.

10 Claims, 5 Drawing Sheets

LOW INTERFACIAL TENSION SURFACTANTS FOR PETROLEUM APPLICATIONS

RELATED APPLICATION

This application is a continuation-in-part of application Ser. No. 12/481,072 filed on Jun. 9, 2009, now U.S. Pat. No. 8,227,383, which claims the benefit of U.S. Provisional Application No. 61/060,004 filed on Jun. 9, 2008. The entire teachings of the above applications are incorporated by reference herein.

FIELD OF THE APPLICATION

The application relates generally to surfactants useful for petroleum applications.

BACKGROUND

A number of problems in the petroleum industry derive from the viscosity, surface tension, hydrophobicity and density of crude oil. Heavy crude oil in particular, having an API gravity of less than 20 degrees, is difficult to transport due to its viscosity, and is difficult to remove from surfaces to which it has adsorbed, due to its hydrophobicity and immiscibility with water. Extra-heavy crude oil or bitumen, having an API gravity of less than 10 degrees, is heavier than water, so that it can sink to the bottom of a water formation, causing subsurface contamination.

The properties of crude oil contribute to the limitations of oil recovery from traditional oil fields. Conservative estimates suggest that 30% of the technically recoverable oil in U.S. oil fields is inaccessible due to the adsorption of the residual oil to porous geologies. Technologies to unlock the oil in these so-called "dead" wells presently involve the use of hot water injections with expensive surfactants, chemistries that are applied to overcome the hydrophobicity of the adsorbed oil so that it can be mobilized.

The properties of crude oil also contribute to the difficulty of environmental remediation following, for example, an oil spill onto a body of water. The high interfacial tension causes the oil to float on the water and adhere to plants, animals and soil. As the aromatic constituents of the oil evaporate, the heavier residues can sink, contaminating the subsurface structures. Current treatment of spilled oil on water surfaces relies on time-consuming and expensive biological degradation of the oil. Thick, adherent crude oil cause environmental problems in the oil fields as well. Oil deposits attached to vehicles and equipment must be cleansed with jets of hot water and caustics.

The viscosity of heavy crude oil makes the substance difficult and expensive to transport to upgrading facilities. Because of its viscosity, a significant amount of energy is required to pump it through pipelines to a refinery. Furthermore, the viscosity affects the speed at which the heavy crude oil can be pumped, decreasing the overall productivity of an oil field. Exploiting certain oil fields or other oil deposits may be economically unfeasible to develop at present because of the transportation-related costs.

Surfactants have been widely used in the petroleum industry to ameliorate the effects of crude oil's physical properties. Surfactant molecules consist of hydrophobic and hydrophilic parts. Their amphiphilic nature allows them to be adsorbed at an oil/water interface, forming micelles that allow the interfacial tension between oil and water to be reduced.

Surfactants are sometimes used for desalting of crude oil. Desalting refers to the process of removing salts from oil, making the oil more suitable for further refining. The salts are typically dissolved in water that is associated with oil, so the removal of water has multiple benefits. The presence of water reduces the energy content of oil, and it carries salts that can harm catalyst performance or cause corrosion. Ethoxylated nonylphenols have been used for desalting of crude oil, but these compounds pose hazards to the environment.

Furthermore, surfactant technologies for the aforesaid petroleum applications typically are expensive or must be used at high concentrations. Additionally, demulsification can prove to be difficult, as these surfactants are designed for emulsifying purposes. Demulsification typically requires added materials and steps to break up the emulsion, which increases the effective cost of use. Furthermore, the salts present in nature can inactivate many surfactant technologies. In addition, other surfactant technologies for petroleum applications are tailored only to oils of a limited composition.

The development of a technology that can provide emulsion and favorable transport properties while maintaining the ability to demulsify on demand, all under variable conditions of salinity, remains unmet in the art. Such a technology would have wide reaching impact across the oilfield chemical sector in applications such as those mentioned above, particularly if the material could be inexpensively produced and could be applied to a variety of oil types.

SUMMARY

The invention relates to the discovery that novel surfactants and surfactant compositions have good to excellent properties in recovering or extracting oil, such as fossil fuels.

Accordingly, in some embodiments, the invention relates to a compound having the formula I:

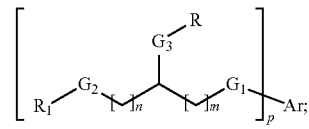

wherein Ar is a substituted or unsubstituted aryl, aralkyl (e.g., benzyl) or heteroaryl group; in some embodiments, Ar is a substituted or unsubstituted aryl or heteroaryl group; preferably a substituted or unsubstituted phenyl group;

p is 1 or 2; preferably 2;

m and n are independently 0, 1, 2, 3, 4, or 5; preferably 1;

each of $G_1$ and $G_2$ are independently absent, O, S, $NR_2$, C(O)O, OC(O), CO, $CONR_2$, or $NR_2CO$; preferably each $G_1$ and $G_2$ are independently O or C(O)O;

each $R_2$ is independently H or a lower alkyl; in some embodiments, the lower alkyl is a C1 to C5 alkyl;

each $G_3$ is independently absent, $(CH_2)_q$ or $G_1$;

q is 1, 2, 3, 4 or 5;

R is a hydrophilic group; preferably the hydrophilic group is COOH, or a hydrophilic polymer; such as a polyethylene glycol or a polypropyleneoxide;

$R_1$ is a saturated or unsaturated hydrophobic aliphatic group; in some embodiments, $R_1$ is $C_5$ to $C_{18}$ alkyl, alkenyl or alkadienyl, preferably a straight chain $C_5$ to $C_{18}$ alkyl;

wherein, when p is 1, Ar is substituted by one or more of $OR_2$, $SR_2$ and $N(R_2)_2$;

preferably, when p is 1 Ar is substituted by OH, SH or $NH_2$.

In one preferred embodiment, $G_1$ is C(O)O, $G_2$ is absent and n is 0. Alternatively, where $G_1$ is O, $G_2$ is not absent, and is preferably O or C(O)O.

A particularly preferred surfactant is a compound having the formula II:

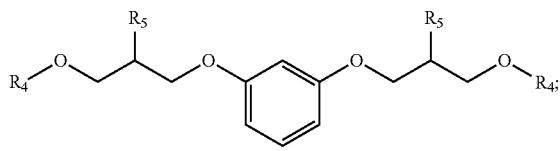

wherein $R_5$ is a hydrophilic group; and
$R_4$ is a saturated or unsaturated hydrophobic aliphatic group.

The invention further relates to a compound having formula III:

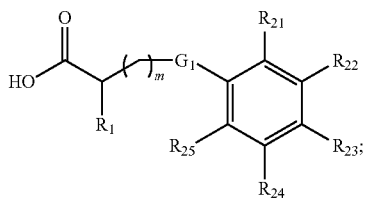

wherein $G_1$ is selected from the group consisting of S, $NR_2$, C(O)O, OC(O), CO, $CONR_2$, and $NR_2CO$; preferably G1 is C(O)O;
each $R_2$ is independently H or a lower alkyl;
wherein, $R_{21}$, $R_{22}$, $R_{23}$, $R_{24}$, and $R_{25}$ are each independently, H, OH, halogen, $C_1$-$C_5$ alkyl, $C_1$-$C_5$ alkoxy, a $C_3$-$C_7$-cycloalkyl group, a phenyl group optionally substituted by hydroxyl, halogen, lower alkyl or lower alkoxy, or Fragment I having the formula shown below:

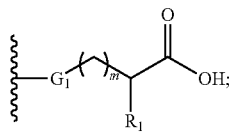

wherein $R_1$, m and $G_1$ are as defined above;
wherein at least one of $R_{21}$, $R_{22}$, $R_{23}$, $R_{24}$, and $R_{25}$ is Fragment I or OH;
or a salt thereof.

A particularly preferred surfactant is a compound having the formula IV:

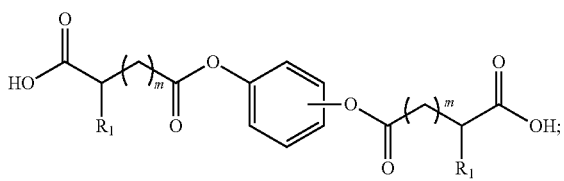

wherein m and $R_1$ are as defined above.
Preferred compounds of formula IV are compounds wherein m is 1 and $R_1$ is a straight chain $C_5$ to $C_{18}$ alkyl.

In other aspects, the invention relates to a composition comprising an aromatic compound and a substituted succinic anhydride, wherein the aromatic compound has the Formula VIII:

Ar-$[G_4]_p$; and the substituted succinic anhydride has the Formula IX:

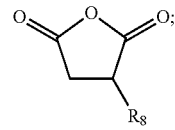

wherein Ar is selected from the group consisting of aryl, arylalkyl and heteroaryl, each optionally substituted;
each $G_4$ is independently selected from the group consisting of $OR_2$, $SR_2$, $N(R_2)_2$, $COOR_2$, $OCOR_2$, $COR_2$, $CON(R_2)_2$ and $N(R_2)_2CO$;
each $R_2$ is independently selected from the group consisting of H and lower alkyl;
$R_8$ is a saturated or unsaturated hydrophobic aliphatic group; and
p is 1 or 2. In some embodiments, each $R_2$ is independently selected from the group consisting of H and C1-C6 alkyl.
In some embodiments, each $G_4$ is independently selected from $OR_2$ or $NR_2$. In additional embodiments, the invention is directed to a method preparing a surfactant composition comprising mixing a compound of Formula VIII with a compound of Formula IX.

In additional embodiments, the invention is directed to a composition comprising an aromatic compound and a substituted succinic anhydride, wherein
the aromatic compound is resorcinol; and
the substituted succinic anhydride has the Formula IX:

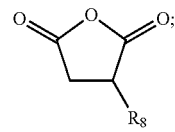

wherein $R_8$ is a saturated or unsaturated hydrophobic aliphatic group. In certain aspects, the resorcinol is m-resorcinol.

In an additional embodiment, the invention is directed to a composition comprising an aromatic compound and a compound of Formula X wherein
the aromatic compound has the formula VIII:

Ar-$[G_4]_p$; and the compound of Formula X is:

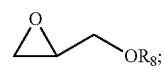

wherein Ar is selected from the group consisting of aryl, arylalkyl or heteroaryl; preferably phenyl or benzyl;
each $G_4$ is independently selected from the group consisting of $OR_2$, $SR_2$, $N(R_2)_2$, $COOR_2$, $OCOR_2$, $COR_2$, $CON(R_2)_2$ and $N(R_2)_2CO$; preferably, $OR_2$ or $N(R_2)_2$;
each $R_2$ is independently selected from the group consisting of H and lower alkyl;
$R_8$ is a saturated or unsaturated hydrophobic aliphatic group; and p is 1 or 2. In some embodiments, the composition comprising Formula X and an aromatic compound further comprises an alkylene oxide, such ethylene oxide or propylene oxide.

In yet another embodiment, the invention is a compound having the Formula (XI):

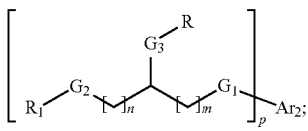

wherein $Ar_2$ is a substituted or unsubstituted phenyl or benzyl;
p is 1 or 2;
m is 1 or 2;
n is 0 or 1;
each $G_1$ is independently selected from the group consisting of OC(O), C(O)O, C(O), C(O)$NR_2$ and $NR_2$CO;
each $G_2$ is absent;
each $R_2$ is independently H or a lower alkyl;
each $G_3$ is independently absent, or $(CH_2)_q$;
q is 1, 2, 3, 4 or 5;
R is a hydrophilic group; and
$R_1$ is a saturated or unsaturated hydrophobic aliphatic group.

In some aspects, the invention is directed to a compound having the Formula XII:

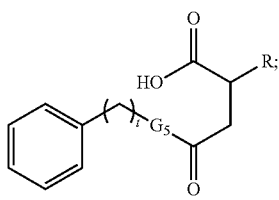

wherein t is 0 or 1;
$G_5$ is O or NH;
and R is as defined above.

In other embodiments, the invention is directed to a compound having the Formula (XIII):

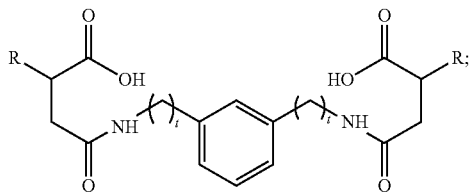

wherein t is 0 or 1 and R is as defined above.

In an additional embodiment, the invention relates to a compound having the Formula XIV:

L-$G_5$-Ar-$G_5$-M;

wherein Ar is aryl, arylalkyl and heteroaryl, each optionally substituted; preferably, Ar is phenyl;
each $G_5$ is independently O or NH;
L is a hydrophilic polyethylene glycol glycidyl ether; and
M is a hydrophobic glycidylalkyl ether.

The invention further relates to a method for extracting oil from an comprising:
(a) adding a compound or composition of the invention to an oil mixture, and
(b) collecting the oil.

An oil mixture is a mixture comprising oil and at least one other component. The oil mixture can comprise oil sands, waterborne oil slicks or oil deposits. Further, the methods of the invention can comprise the additional steps of adding water or transporting the mixture via a pipeline. In another embodiment, the compounds and compositions of the invention can be used in methods of degreasing machinery, such as those used in oil or bitumen production.

DETAILED DESCRIPTION

General Formulations

Figure 1:
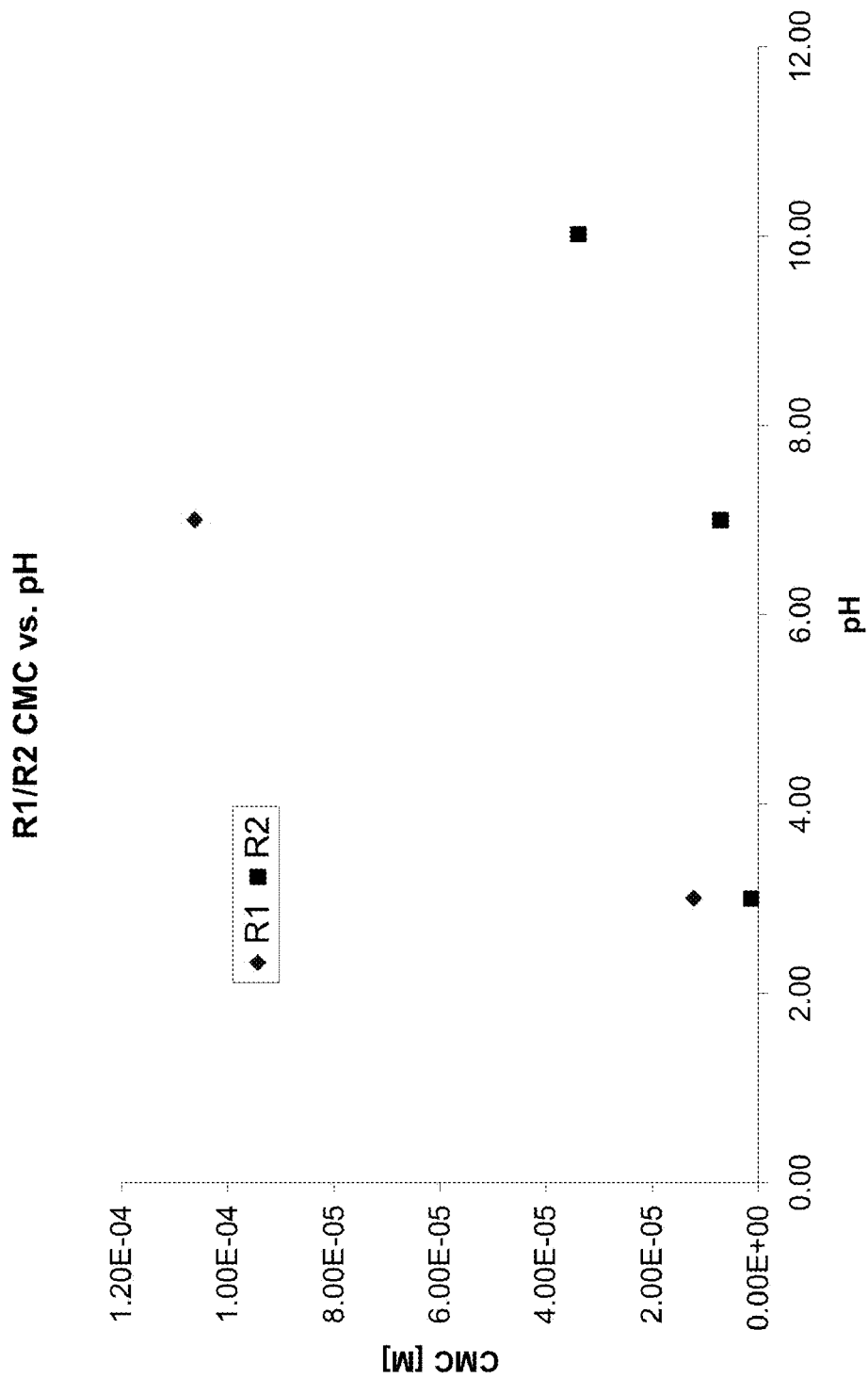
FIG. 1 illustrates examples of critical micelle concentration of compositions (a 1:1 composition of m-resorcinol and alkylated succinic anhydride (Eka SA 210 brand alkylated succinic anhydride) and a 1:2 composition of m-resorcinol and alkylated succinic anhydride of formulas shown below; labeled R1 and R2, respectively).

Disclosed herein are compositions, systems and methods related to ultra-low interfacial tension ("IFT") surfactants for applications in the petroleum industry. In certain embodiments, the present disclosure is based on the discovery that certain ester surfactants and compositions comprising resorcinol and alkenylated succinic anhydride are highly effective surfactants for petroleum applications, and can be used as additives in petroleum processing, oil sands extraction and processing, environmental remediation, enhanced oil recovery, and the like.

In one embodiment, compositions of particular use in these systems and methods can include at least one compound of the formula (V):

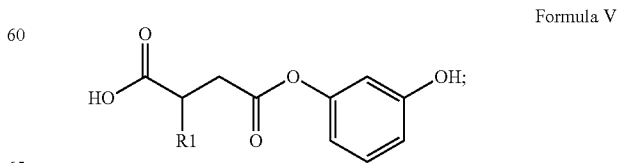

Formula V wherein $R_1$ is a hydrophobic group as defined above.

In alternate embodiments, compositions of particular use in these systems and methods can include at least one compound of formula (VI):

Formula VI

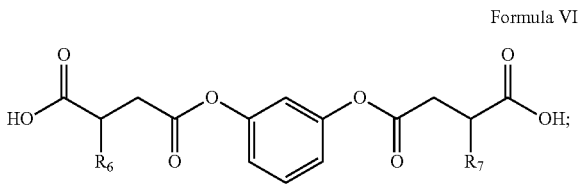

wherein $R_6$ and $R_7$ are each independently a hydrophobic group.

In one embodiment, compositions of particular use in these systems and methods can include at least one compound of the formula (VII):

Formula VII

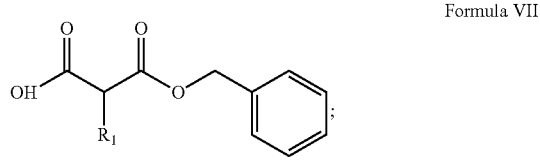

wherein $R_1$ is as defined above for Formula I.

In yet another embodiment, the surfactant compound has the Formula XI, XII or XIII as shown above.

The invention also encompasses compositions comprising an aromatic compound having the Formula VIII and a substituted succinic anhydride having the Formula IX. In an additional embodiment, the invention is directed to compositions comprising an aromatic compound having the Formula VIII and an ether compound having the Formula X. The succinic anhydride of Formula IX and the compound of Formula X are substituted with a hydrophobic aliphatic group. In some aspects, the hydrophobic aliphatic group is selected from the group consisting of alkyl, alkenyl, alkadienyl, alkynyl, cycloalkyl, cycloalkenyl, aryl and heteroaryl. In certain embodiments, the aromatic compound comprises an optionally substituted benzyl or optionally substituted phenyl core. In additional aspects of the invention, $G_4$ is selected from the group consisting of $OR_2$ or $N(R_2)_2$. In yet another embodiment, the invention is a composition comprising resorcinol (for example, m-resorcinol) and a succinic anhydride having the Formula IX.

The compounds and compositions described herein can be used as surfactants. The inventive surfactant compounds comprise an aromatic core with pendant aliphatic hydrophobic and hydrophilic portions. The inventive compositions comprise an (i) aromatic compound and (ii) a substituted succinic anhydride or a substituted ether which each are substituted with hydrophobic groups. As will be understood by one of skill in the art the hydrophobic portion of the surfactant compound or composition can comprise one or more hydrophobic groups or substituents. Similarly, the hydrophilic portion of the inventive compounds can comprise one or more hydrophilic groups or substituents. Attached aliphatic hydrophobic portions or groups can consist of linear or branched, saturated or unsaturated, substituted or unsubstituted higher alkyls. For example, the hydrophobic group can be derived from alkanes with or without internal or terminal alkenes. In some embodiments, the higher alkyl comprises at least five carbon atoms. In other embodiments, the higher alkyl is a $C_5$ to $C_{18}$ alkyl, alkenyl or alkadienyl, or C5 to C20 alkyl, alkenyl or alkadienyl, or C8 to C20 alkyl, alkenyl or alkadienyl. Hydrophilic portions or groups can be an ionizable groups, including, for example, amines and carboxylic acids. Hydrophilic groups also include hydrophilic polymers, including, but not limited to, polyalkylamine, poly(ethylene glycol), poly(propylene glycol) or polyethylene glycol/polypropylene glycol copolymers. Nonionic hydrophilic materials such as polyalkylamine, poly(ethylene glycol) or poly(propylene glycol) can be used to increase hydrophilicity or aid stability in salt solutions.

In some embodiments, the aliphatic groups include saturated or unsaturated carbon chains, preferably between five and twenty units in length, or five and eighteen units in length, or eight and twenty units in length, or hydrogen. The carbon chains can optionally be unsaturated and, when present, reside anywhere along the carbon chain.

The aromatic core of the inventive compounds or the compounds in the compositions (e.g., Ar or $Ar_2$ as described above) can be carbocyclic or heterocyclic, monocyclic or polycyclic, substituted or unsubtstituted. Preferred aryl groups can be derived from resorcinol, phenol, phenyl amine, creosol, benzyl alcohol, benzyl amine, naphthalene, anthracene, pyrene, tetrahydronaphthyl, indanyl, idenyl or the like. Heteroaromatic structures such as thiophene, selenophene, silole, pyrrole, pyridine, furan, imidazole, indole, pyrazinyl, pyrimidinyl, pyrazolyl, imidazolyl, thiazolyl, oxazolyl, isooxazolyl, thiadiazolyl, oxadiazolyl, furanyl, quinolinyl, isoquinolinyl, benzimidazolyl, benzooxazolyl, quinoxalinyl, and the like can also be used as the aromatic core. The term "substituted" refers to substitution by independent replacement of one or more of the hydrogen atoms thereon with substituents including, but not limited to, —OH, —$NH_2$, —NH—$C_1$-$C_{12}$-alkyl, —O—$C_1$-$C_{12}$-alkyl, —SH, and —S—$C_1$-$C_{12}$-alkyl, C1-C12 alkyl, and C1-C12 alkenyl.

In certain aspects of the invention, the hydrophilic portion of compounds of the invention (e.g., R as described above) is one or more ionizable carboxylic acid groups, which groups, in some embodiments, can make up the totality of the hydrophilic portion. By themselves, the carboxylic acid portions are not enough to effectively stabilize emulsions formed by the mixture of a waterborne suspension of the disclosed surfactant compounds. Addition of a small amount of base (greater than about pH 8 or between a pH of about 8 and about 9) is sufficient to ionize, leaving a more active, emulsion-forming material. The emulsion can later be destabilized by adding acid to the material, removing the charge stabilization and splitting the two incompatible phases.

Changing pH is one method of enabling and disabling the surfactant behavior; however, compounds of formula (I) and formula (III) are typically unstable hydrolytically.

In other aspects of the invention, the hydrophilic portion of compounds of the invention is one or more polymers or copolymers containing ether groups. These polymers will impart the compounds with a cloud point. The compounds will display solubility in water at temperatures below the cloud point and, as a consequence, will be able to emulsify oil. However, upon increasing the temperature over the cloud point, the compounds will become less soluble in water and will lose their emulsification properties. This behavior is reversible because no functional groups are cleaved in the process. An example of compounds exhibiting this behavior are compounds having the Formula (XIII).

Some examples of compounds of Formula XIII can be obtained by reacting:

Aromatic (primary or secondary) amines with polyetherglycidyl ethers. Examples of amines are: ortho, meta or para phenylene diamine. The polyether can be polyethyleneglycol diglycidyl ether. Another example of these compounds can be obtained by reacting an aromatic diamine with a hydrophilic polyethylene glycol glycidyl ether and a hydrophobic glycidyl alkyl ether. The resulting product has comprises a rigid aromatic unit in the middle and 2 linear groups hanging from it, one of the groups being hydrophilic and the other hydrophobic.

The tunable behavior of the inventive surfactants and surfactant compositions has utility for petroleum-related applications. For example, if the residence time of the oil in a pipeline is known or can be estimated, the amount of base can be calculated and added with the surfactant to cause decomposition begin in the pipeline and separation to occur immediately after the emulsion reaches its destination. This has the benefit of decreasing residence time in a storage facility while the emulsion breaks.

Applications

Environmental Remediation

By taking advantage of the low IFT behavior of the surfactant compounds and compositions disclosed herein, such surfactant compounds and compositions can be suitable for applications where undesired petroleum products pose an environmental problem. Oil cleanup using surfactant compounds and compositions may be required for two different types of contamination. First, as an oil slick dispersant, the surfactant compounds and compositions described herein can be used on waterborne slicks, acting as a dispersing agent. The surfactant compounds and compositions will act to disperse the oil into the water body itself and encourage biodegradation through natural decomposition means. Additionally, a solution of surfactant or surfactant composition can be used to remove physiosorbed crude or refined oils from inorganic rocks, sand, or other substrates as an emulsion.

Oil Sands Extraction

Oil sands comprise heavy petroleum products coating sand and clay, an assemblage that is similar to certain artificial composites that are formed during a man-made oil spill, as described above. The systems and methods described herein can be useful for extracting bitumen from the other components of the tar sands material. Currently, mined oil sands are extracted using hot water, a process that causes the less dense bitumen to flow off the sand and float to the surface of a settling tank. This so-called "primary froth" is contaminated with various materials derived from the mined products (solid particles, clay, and sand). Current froth treatment utilizes naphtha, a valuable fraction of purified petroleum, to dilute the bitumen and decrease the viscosity to the point of flowability. This allows solids and water to be removed by settling and centrifugation methods. By using an aqueous solution of surfactant or the compositions described herein as the dilution medium instead of naphtha, the latter solvent can be replaced with water and surfactant, thus decreasing the cost of purifying the froth. Additionally, when the surfactant-diluted bitumen is recovered from the water, the hydrophilic portions associated with the froth (clay, water, salts) preferentially partition to the water phase and be separable from the bitumen.

Use of surfactants and surfactant compositions in accordance with these systems and methods can further be applied to other aspects of the extraction process, for example in the oil sands strip mining or in-situ operations, where the ability to emulsify the petroleum component of the oil sands ore may enhance the efficiency or economy of separating the bitumen from the insoluble byproducts.

Oil Field Transport Emulsions

Transporting petroleum precursors for further processing is a necessary, though expensive, part of obtaining usable crude oil. When petroleum is obtained as a heavy crude, it needs to be transported to an upgrading facility for conversion to useful petroleum products. Typically, pipeline transport is the most economical means to accomplish this. When oil sands are used as precursors in the production of synthetic crude oil, they are transported for further processing after extraction and froth treatment through pipelines as a naphtha-diluted bitumen so that they can undergo further upgrading processes, including cracking and coking, amongst other standard refining operations. For these types of applications in the petroleum and tar sands industries, the heavy oil or oil precursor materials (respectively) may be transported through pipelines as oil-in-water mixtures or emulsions. It is understood that more viscous matter being sent through pipelines has a greater resistance to flow and consequently requires more energy to move an equivalent distance. Hence, decreasing the viscosity of the flowable matter decreases the amount of pumping energy required, and potentially improves the transit time and the productivity of the overall process. Mixing water with crude oil or bitumen can decrease the viscosity of these latter substances towards the viscosity of water, but only if a water-continuous emulsion is created. The described low IFT surfactants and surfactant compositions can compatibilize oil and water into an emulsion that can be pumped with greatly decreased energy requirements and/or increase the throughput of crude oil or oil precursors to their destinations.

Auxiliary Petroleum Applications

There also exist many other opportunities in the oilfield chemical sector for degreasing applications, as can be accomplished with the systems and methods disclosed herein. Periodically, machinery used in oil and bitumen production must be cleaned for maintenance and performance reasons. With petroleum production heading towards heavier crude reserves, the need for an effective degreaser becomes even more acute: exposure to heavier crude oils results in thicker, more adherent oil residues that must be removed during the cleaning/degreasing processes. The described low IFT surfactants can be an active ingredient in an industrial degreasing formulation for these purposes.

Enhanced Oil Recovery (EOR)

Tertiary oil recovery, also known as "enhanced" or "improved" oil recovery, makes use of low IFT surfactant and surfactant compositions to produce oil from wells that have stopped producing of their own accord. Injection of a low IFT surfactant into one of these less productive wells can stimulate production from the residual oil left adhered to the surface of porous rocks. The compounds and compositions described herein are useful as low IFT surfactants for EOR. Due to the temperatures and residence time underground, certain esters made in accordance with the invention may be too unstable for these applications. In addition, the resident acid groups on the compound of formula (II) are highly sensitive to saline commonly found in well formations.

The compound of formula (II) may be particularly suitable for EOR applications:

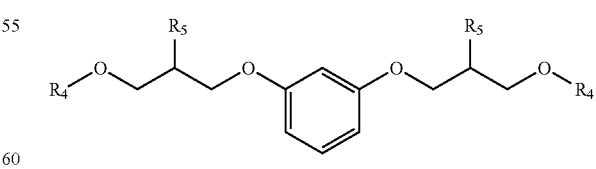

$R_4$ and $R_5$ are as defined above.

In some embodiments, $R_4$ can include a linear or branched carbon chain consisting of five to eighteen carbon atoms. Advantageously, substituent R4 can be a saturated or unsaturated carbon chain consisting of five to eighteen carbon atoms.

In some embodiments, $R_5$ can include water soluble oligomers such as poly(ethylene glycol) or poly(propylene oxide). By using a small poly(ethylene glycol) as the hydrophilic portion the substituent $R_5$, and all ether connectivity, the molecule of formula (II) may desirably withstand the temperature and salinities found underground for the requisite time period.

In some aspects, the compositions comprising an aromatic compound of Formula VIII and succinic anhydride having the Formula IX (such as, resorcinol and succinic anhydride having the Formula IX) can be used in EOR applications as described herein.

EOR techniques in accordance with these systems and methods can improve the mobility of oil while making the rock reservoir water-wet to improve its permeability and allow for the recovery of oil at an increased rate. EOR systems and methods can involve using thickening polymers that can self-assemble at the oil surface and act as an efficient emulsifier. In embodiments, aqueous fluids can be designed that will increase sweep efficiency and percent recovery for EOR.

It is understood that the efficiency of a displacing fluid can be defined by the mobility ratio as well as the capillary number. The mobility ratio is indicated by Equation 1.

$$M = \frac{k/\mu(displacing fluid)}{k/\mu(displaced fluid)} \quad \text{Equation 1}$$

In Equation 1, k is the permeability of the media and $\mu$ is the viscosity of the fluid. The mobility ratio indicates the sweeping efficiency of a displacing fluid. A mobility ratio <1 can mobilize oil while >1 cannot. The capillary number is indicated by Equation 2.

$$Ca = V\frac{\mu}{\gamma} \quad \text{Equation 2}$$

In Equation 2, V is the characteristic velocity, $\mu$ is the viscosity of the displacing fluid and $\gamma$ is the IFT. The capillary number is a dimensionless number that characterizes the relationship of viscosity and IFT of two immiscible fluids. Low capillary number indicates capillary forces will determine the flow through the rock reservoir. The percent oil recovery increases as a function of the capillary number of a displacing fluid. Fluids such as water that have a high mobility ratio and low capillary number will take the least tortuous path through the formation and therefore are poor displacing fluids.

It is to be understood that a surfactant can give a low mobility ratio with a high capillary number as a single component system even in low concentrations. Although in theory, either a low mobility ratio or high capillary number can give 100% oil recovery, this is not true in practice. In embodiments, these systems and methods can provide for a cost effective and efficient method for EOR that improves both the mobility ratio and capillary number of the displacing fluid. In embodiments, an amphiphilic polymer can be used to act as a thickener in the displacing aqueous phase which can self-assemble onto the surface of oil and act as a surfactant in the oil phase.

EOR processes must be robust enough to survive the subterranean environments that typically see temperatures in excess of 100° C. while salinity and dissolved solids can vary greatly. In embodiments, polymers are selected that can withstand high temperatures without degrading. For example, hydrophilic groups can shield the polymer from changes in water chemistry including multivalent cations. Or, for example, the polymer can be diluted and delivered in a brine solution which can significantly reduce cost. In embodiments, the self-stabilizing polymeric surfactant can serve to hinder precipitation unless in the presence of a strong hydrophobe. In embodiments, for example, the stability of the polymer surfactant is only broken down in the presence of hydrophobic compounds such as oil. At this point, a selected polymer would cease to behave as a polymer slug and would become more like a surfactant. It is understood that the presence of a hydrophobe would destabilize the selected polymer, and it could undergo a conformation change to a more stable structure that could effectively emulsify oil. A hydrophobic component of the selected polymer could penetrate the oil-water interface and effectively reduce the IFT. The polymer could also have the effect of slightly reducing the viscosity of the oil in the surrounding area.

In embodiments, these systems and methods can include stimuli-responsive surfactants templates produced in polymeric form for EOR applications. In embodiments, a polymer could emulsify or demulsify due to a certain stimulus such as pH or temperature. Demulsification, for example, could be used to improve oil reclamation in an ex-situ process.

In embodiments, polymeric agents such as polyimide-amine salts of styrene-maleic anhydride (SMA) copolymers could be used as surfactants in accordance with this disclosure. In one embodiment, a SMA copolymer having pendant tertiary amine groups containing a salt-forming tertiary nitrogen atom neutralized to the extent of at least about 75 percent with mono-carboxylic acids, having for example an aliphatic chain of at least about 8 carbon atoms, could be used. In embodiments, the polyimide-amine salts useful for EOR can also contain mixed imides, resulting, for example from the reaction of dialkylaminoalkylamines and monoalkyl amines, or mixed imide-amides resulting from the reaction of dialkylaminoalkylamines and dialkylamines. In embodiments, salts can be prepared by converting the anhydride rings of styrene-maleic anhydride copolymers to polyimides containing pendant tertiary amine groups. These pendant tertiary amine groups can be neutralized with monocarboxylic acids to form salts that have useful properties for EOR. Mixed imide forms of these salts can be obtained by reacting primary alkylamines with a minor portion of the anhydride groups of the styrene-maleic anhydride copolymer. Similarly, mixed imide-amide forms of the salts can be obtained by reacting a minor portion of the copolymer anhydride groups with secondary dialkylamines.

In embodiments, useful polymers in accordance with these systems and methods could be formed from polyimide-amine acid salts of styrene-maleic anhydride copolymers containing pendant tertiary amine groups that are neutralized to the extent of at least about 75 percent with sufficient monocarboxylic acid having an aliphatic carbon-to-carbon chain of at least about 8 carbon atoms, preferably as a terminal group. In embodiments, a styrene-maleic anhydride copolymer can be imidized to the extent of at least about 65 percent up to about 100 percent of its anhydride groups, and neutralized with a dialkylaminoalkylamine to the extent of about 75 percent to 100 percent, with the long chain monocarboxylic acid. The styrene-maleic anhydride copolymer polyimide-amine acid salts can also contain imide groups or amide groups up to the extent of about 35 percent of its anhydride groups by reaction with a primary or secondary alkylamine, for instance, of about 8 to 30 carbon atoms. In embodiments, the ratio of styrene to maleic anhydride in the styrene-maleic anhydride copolymer of this invention can be in the range of about 0.1:1 to 5:1, preferably about 0.5:1 to 2:1, and most preferably about 1:1. In embodiments, the styrene-maleic anhydride copolymer molecular weight can vary from about 400 to 5,000, preferably from about 1,000 to 5,000, and often is in the range of about 1,400 to 2,000. In embodiments, long hydrophilic chains can be attached to the copolymer backbone.

Polymers such as those disclosed herein can be used to formulate surfactants that have multipoint interaction with aromatic heavy oil, thus yielding utility in EOR. In embodiments, the polymers can be modified, for example by adding hydrophilic chains (e.g., polypropylene oxide/polyethylene oxide polymeric chains) to promote pulling emulsified oil drops into water.

Desalting

Desalting refers to the process of removing salts from oil, making the oil more suitable for further refining. Salts, including magnesium chloride, sodium chloride and calcium chloride can be found in crude oil. If allowed to remain in the crude oil during the refinery operation, the salts can dissociate and the chloride ion can ionize to form hydrochloric acid, which, along with various organic acids found in crude oil, contributes to corrosion in refinery equipment. In addition, other metal salts (e.g., potassium, nickel, vanadium, copper, iron and zinc) can be found in the crude oil, also contributing to fouling of the equipment and end-product degradation. Crude oil also contains emulsified water, which contains dissolved salts.

Desalting crude oil takes advantage of the fact that the salts dissolve in a water phase, which is separable from the oil phase. Crude oil naturally contains water in emulsion, as mentioned above. For certain techniques of desalting, additional water may be added to the oil (e.g., in an amount between 5-10% by volume of crude) so that the impurities can further dissolve in the water. The water-in-oil emulsion can be broken with the assistance of emulsion-breaking chemicals and/or by exposing the emulsion to an electrical field that polarizes the water phase, so that the water phase bearing the impurities separates from the petroleum phase. Ethoxylated nonylphenols are a class of nonionic surfactants that have been used for desalting crude oil according to these principles.

The surfactant compounds and compositions disclosed herein can facilitate the demulsification of the water-in-oil emulsion, so that the oil phase separates from the water phase, with the water phase carrying the soluble impurities (i.e., the salts). In embodiments, the hydrophilic portion of the surfactant compound and compositions can include one or more ionizable carboxylic acid groups that can be ionized at a basic pH (e.g., >8) to produce an emulsion-sustaining material as described above. To destabilize the emulsion, acid may be added, removing the charge stabilization and allowing the two phases to segregate from each other.

Sludge and Contamination Removal

In the field, the well outflow stream is first separated into its three components: natural gas, crude oil and produced water. The produced water and crude oil can form a stable emulsion that can interfere with ready separation of these two components. Furthermore, water can also be introduced into an oil-bearing formation to apply pressure to the oil within the formation to keep it flowing. Oil that is recovered under these circumstances also contains a water fraction, typically dispersed as a stable emulsion. This stabilized layer of water in oil, known as the "rag layer," actually includes multiple phases, such as solid-in-oil dispersions, water-in-oil emulsions, and oil-in-water-in-oil emulsions.

With heavy oils, there can be finely divided mineral solids or other materials within the production stream that can act as emulsifiers. For example, materials such as asphaltenes and high naphthenic acids, along with submicron sized solid particles such as silica, clay or other minerals can stabilize water-in-oil emulsions where the heavy crude oil fluid comprises the continuous phase.

Asphaltenes, paraffinic waxes, resins and other high-molecular-weight components of heavy crude exist in a polydisperse balance within the emulsified heavy crude fluid. A change in the temperature, pressure or chemical composition can destabilize the polydisperse crude oil. Then the heavy and/or polar fractions can separate from the oil mixture into steric colloids, micelles, a separate liquid phase, and/or into a solid precipitate. Asphaltene precipitation causes problems all along the crude oil process. Asphaltene precipitation becomes increasingly problematic when crude oil is processed, transported, or stored at cooler temperatures, because the heavier components of crude oil (e.g., asphaltenes and naphthenic acids) that remain dissolved in the heavy crude under high temperatures and pressures are no longer supported in that state as the conditions change. When the heavy crude oil cools to ambient atmospheric temperatures, these components can precipitate out of the crude oil itself and lodge at the bottom of a storage vessel or tank to form a viscous, tarry sludge. These components also become available as emulsifying agents to sustain the water-in-oil emulsions formed as part of the rag layer. The rag layer has a higher density than light crude, so that it tends to sink to the bottom of storage vessels along with the heavy oil components and associated clay/mineral solids, contributing to the buildup of oil sludge, a thick waste material formed from the various deposits sedimenting out from a crude oil mixture. Sludge forms when heavier components of crude oil separate from the liquid hydrocarbon fractions by gravity and sink to the bottom of an oil tank or other containment vessel. Any given storage vessel can contain a significant amount of sludge, which can diminish storage space for useful crude oil and which can otherwise reduce the efficiency of storage tank operation. Sludge may also require removal if the storage vessel is to be maintained, repaired or inspected.

In the course of activities related to onshore production, offshore production, transportation, refining, and use of oil, spills and other undesirable releases of hydrocarbons can occur. Contaminated sediments are formed when oily materials contact sand, soil, rocks, beaches, and the like. In some cases, the spills are from long term gradual releases at industrial sites, and in other cases the spills can be from catastrophic accidental discharges. In either event, the contaminated soils will require remediation to prevent further environmental damage. The contaminated soil can be in the form of oil-soaked sediments, or water/oil mixtures with solids, including emulsions. Since the contaminated soils have features in common with tank bottoms sludges, the same treatment processes may be applied to both cases.

In accordance with these systems and methods, the inventive surfactant solution and compositions comprising an amphiphilic surfactant can be used to emulsify heavy crude oil components that have settled as a sludge at the bottom of the oil containment vessel. Such a surfactant or surfactant composition can be injected into the sludge, thereby forming an oil-in-water emulsion comprising the heavy crude oil components of the sludge, which emulsion can then be removed from the oil containment vessel, thereby desludging it. In embodiments, the sludge to be treated comprises an oil-contaminated sediment that was created by accidental discharge of hydrocarbons onto the ground or a body of water. In embodiments, the sludge to be treated comprises asphaltenes, or it comprises a water-in-oil emulsion.

In embodiments, the aqueous surfactant and/or surfactant compositions includes a switchable, "smart" surfactant, which can be injected as an aqueous solution into an oil storage vessel to emulsify the heavy oil sludge into the water phase with minimal agitation. Establishing water as the continuous phase of the emulsion for the sludge can decrease the sludge viscosity so that it can be pumped out of the storage vessel into an alternate containment system. For example, the sludge-in-water emulsion can be directed to a distinct separation vessel, where the emulsion can then be broken, yielding a phase-separate two-component system comprised of crude oil fractions suitable for further refining and recovered water suitable for reuse in similar or other projects.

In embodiments, several steps will be required for the surfactant system. First, the surfactant or surfactant composition will be injected into the heavy oil sludge (including the rag layer), so that the surfactant or surfactant composition can destabilize the heavy oil-water interface to invert the emulsion into the water phase. In this initial phase, an amphiphilic, water-soluble polymer can be used that is effective at low concentrations. After this is accomplished, the resulting water emulsion can be removed from the subject vessel and relocated, for example to a separation vessel. This may take place as a separate step after the first step has been completed. In other embodiments, however, this can take place during the first step. For example, the water emulsion can be siphoned off as it is formed. As a final step, the water emulsion containing the stabilized oil droplets can be demulsified. A change in the conditions of the water emulsion can change the conformation of the surfactant, so that it breaks into an oil-soluble component and a water-soluble component. The oil-soluble component thus demulsifies the heavy oil droplets, while the water-soluble component remains in the water phase. Surfactant molecules can be designed so that the water-soluble byproduct is non-toxic and environmentally safe. The emulsification and/or separation processes might be carried out at temperatures above ambient, to facilitate flow and emulsification or to cause switching of the surfactant properties.

Oil Shale Extraction

In embodiments, the systems and methods disclosed herein can be adapted for extracting hydrocarbons from the kerogen in oil shale sources. In embodiments, theses systems and methods can mobilize kerogen to allow retorting processes to be carried out at lower temperatures than are presently required. Processes for treating oil shales can include (A) acid etching, (B) kerogen decomposition, and (C) extraction with kerogen-based surfactants.

First, the oil shale sedimentary rock can be treated, or etched, with aqueous acid solutions. As examples, organic or inorganic acids can be used. Preferably inorganic mineral acids (hydrochloric, sulfuric, phosphoric) or waste acids are used due to lower costs. In embodiments, exposing the oil shale rock material (e.g., limestone, nahcolite, etc.) with acid for a short period of time and at relatively low temperatures can introduce porosity, improving its permeability to fluids that will contact it during the subsequent steps of the method. In embodiments, the acid treatment may be applied to ex-situ (i.e., mined) oil shale. In other embodiments, the acid treatment may be applied to in-situ oil shale.

Second, the oil shale can be treated with a solution that induces fracturing or decomposition of the kerogen molecular structure. In embodiments, the solution can contain radical-generating chemicals and or electron transfer generators. The radical and electron transfer generators will break carbon-carbon and ether bonds. This will fractionate the kerogen-producing fragments having lower molecular weights. In embodiments, the acid etching and kerogen decomposition are done concurrently.

In embodiments, examples of radical/electron generators can include hydrogen peroxide, ammonium or sodium persulfate, organic peroxides such as benzoyl peroxide, organic azo compounds such as azo-bis isobutyronitrile, zero valent iron, Fenton's reagent, and the like. Not to be bound by theory, these reagents can work by breaking bonds (carbon-carbon or ether), resulting in kerogen with lower molecular weight. The goal with this step is that in the next treatment the surfactants will be able to emulsify at least part of the kerogen (the part with lower molecular weight) and the other part with higher molecular weigh will have higher mobility. The mobility of the kerogen is thereby increased because the molecular weight will be lower than the original condition, and also some interactions between the rock and kerogen have been destroyed by the chemical treatment.

After exposure to the radical/electron generator agents, there can be 2 products. One product is an emulsion, mixture, or suspension of the lower MW kerogen fractions (degraded kerogen) in water. No retorting of this product is required. The degraded kerogen is extracted with an aqueous surfactant solution and subsequently separated form the surfactant/water solution by use of switchable surfactants. The recovered kerogen will enter the typical refining process. The second product can be the residual rock containing the higher MW fractions of kerogen. This rock will be retorted but at lower temperatures than currently used for oil shales. The recovered kerogen will enter the typical refining process.

As a third step, the oil shale can be treated with surfactants designed to have high affinity for kerogen. In embodiments, the surfactants will preferably have a hydrophilic-lipophilic balance value higher than 10 in order to be able to form oil-in-water (O/W) emulsions, and the surfactants can include ionic or non-ionic types. In embodiments, the structure of the surfactant can be aliphatic and, preferably with a cyclic aliphatic structure. The surfactants can preferably be temperature or pH switchable. In embodiments, the surfactant can be made from fractions or fragments of kerogen that have been recovered from oil shale. In embodiments, the surfactant can be made from structures that mimic the components of kerogen. Some examples are compounds obtained by modifying lignin by reacting some of the hydroxy groups in the lignin with groups that provides more hydrophilic characteristics. Some of these groups can be carboxy terminated polyethylene oxide, succinic acids, etc.

Kerogen fragments or fractions can be isolated from oil shale by extraction or distillation, optionally in concert with thermal or chemical decomposition of the kerogen to improve mobility or solubility. The fragments or fractions, once isolated, can be modified with functional groups to convert them to surfactants with an affinity for kerogen. In embodiments, these modifications can include hydrophilic modifications, such as ethoxylation, propoxylation, oxidation, sulfonation, phosphorylation, and modification with other polar groups.

In embodiments, the surfactants can be suspended in an aqueous mixture, so that they can emulsify part of the fractionated kerogens, for example, those hydrocarbons having lower molecular weight. In embodiments, the surfactants can increase the mobility inside the rock formation of the remaining kerogen fractions having higher molecular weights. This extraction or mobilization can be aided by the surfactant reducing the interfacial tension between the kerogen fragments and the water phase, or by solubilizing the kerogen fragments. The extraction, chemical treatment processes can are be aided by heating the formation. An object of the invention is to reduce the total energy requirements of recovering kerogen.

Use of the foregoing steps can treat oil shale so that lower temperature retorting mechanisms can be used for extracting useful hydrocarbons from the kerogen in the rock. These techniques can be adapted for use with surface processing or in-situ extraction methods.

The invention is illustrated by the following examples which are not meant to be limiting in any way.

EXAMPLES

Materials

All materials were obtained from Sigma-Aldrich with the exception of Eka SA 210 that was supplied by EKA Chemicals, Inc., Marietta, Ga. 30062, USA. ERISYS GE-7: CVC Thermoset Specialties, Moorestown, N.J. 08057 USA.

Example 1

Surfactant Compositions Comprising an Aromatic Compound and Alkylated Succinic Anhydride The composition was prepared as follows:
A 300 ml bomb is charged with resorcinol (5 g, 48 mmol) and Eka SA 210 brand alkylated succinic anhydride (100% C18 chain, 16.8 g., 48 mmol). To this, acetone (150 ml) was added, the vessel is sealed and heated to 80 C for 16 hours. After the reaction is complete, acetone is removed under vacuum. The product was analyzed by IR which showed only a small fraction of disappearance of the anhydride peak and small formation of acid (hydrolysis of the anhydride group).

Example 2

Surfactant Compositions Comprising an Aromatic Compound and Alkylated Succinic Anhydride The composition was prepared as follows:
A 300 ml bomb reactor was charged with resorcinol (5 g, 48 mmol) and Eka SA 210 (33.7 g, 96 mmol). To this, acetone (150 ml) was added, the vessel sealed, and heated to 80° C. for 16 hours. Then, acetone was removed under vacuum. The product was analyzed by IR which showed only a small fraction of disappearance of the anhydride peak and small formation of acid (hydrolysis of the anhydride group). NMR of the product indicated that attachment of the anhydride to the resorcinol was negligible.

Example 3

Proposed Synthesis of Compounds of Formula (II)

Compounds having the structure of formula (II) may be synthesized as follows:
A 300 ml bomb is charged with resorcinol (5 g, 48 mmol) and glycidyl hexadecyl ether (28.6 g, 96 mmol). To this, acetone (150 ml) is added, the vessel sealed, and the mixture heated to 80° C. for 16 hours. After this first addition, the material is isolated and dried under vacuum. The alcohol moieties created by the epoxide ring opening is used as initiators in an ethylene oxide polymerization to create a hydrophilic portions on the surfactant, under standard ethylene oxide polymerization conditions. The scheme below illustrates this Synthesis III:

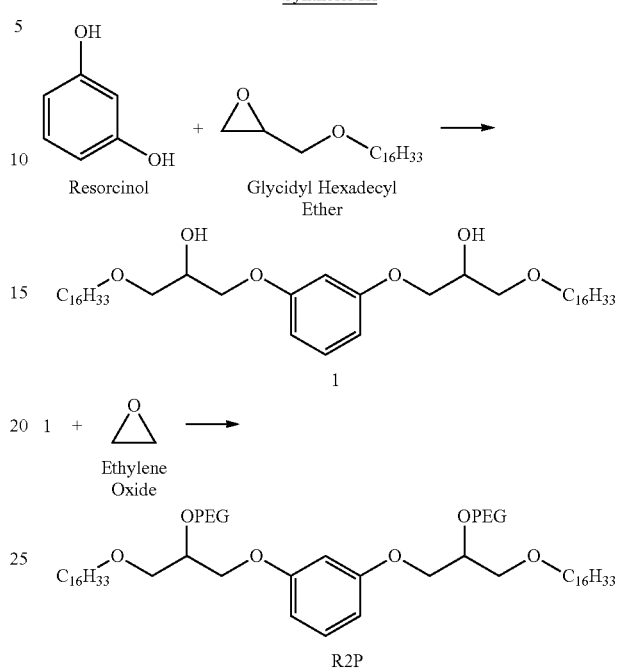

Example 4

Proposed Synthesis of Compounds of Formula (II)

Compounds having the structure of formula (III) may be synthesized as follows:
A 300 ml bomb is charged with resorcinol (5 g, 48 mmol) and glycidyl hexadecyl ether (14.3 g, 48 mmol). To this, acetone (150 ml) is added, the vessel sealed, and the mixture heated to 80° C. for 16 hours. After this first addition, the material is isolated and dried under vacuum. The alcohol moieties created by the epoxide ring opening is used in the next reaction to add hydrophilic portions to the molecule. Compound I is dissolved in acetone and heated to 80° C. to complete the reaction without the need for an ethylene oxide polymerization. The scheme below illustrates this Synthesis IV.

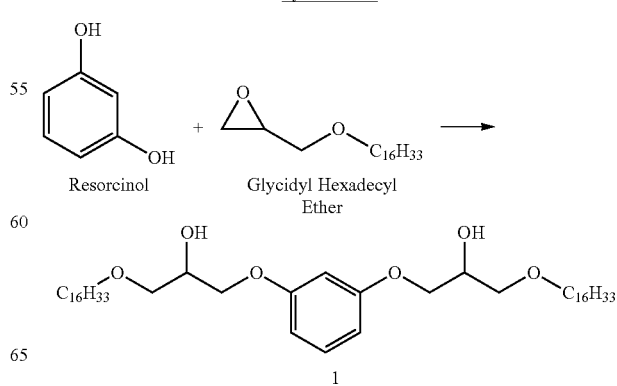

-continued

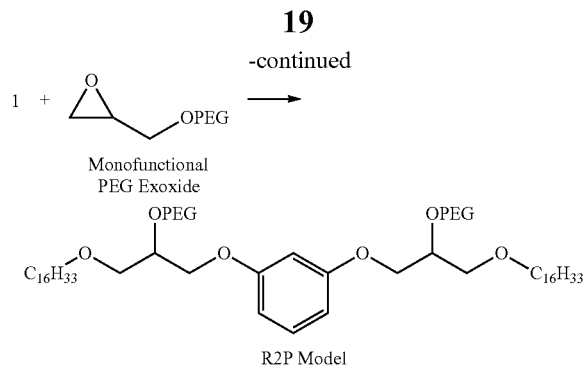

Monofunctional PEG Exoxide

R2P Model

Example 5

Critical Micelle Concentration

Critical micelle concentration (CMC) is an important metric with surfactant systems. It is defined as the minimum surfactant concentration that will form micelles. Below this amount, the molecules exist only in a non-aggregated form. Additionally, this number also represents the constant concentration of monomeric molecules in solution. Effectively, it describes a lower limit to usage and is a good first approximation to formulation content.

A series of aqueous surfactant dilutions were prepared in deionized water with concentrations between 20 µM and 200 mM. The water surface tension at 22° C. was measured on a KSV 702 tensiometer using the Du Nouy ring method. Measured surface tensions were plotted against concentration and linear regression analysis was used to find the inflection point denoting the critical micelle concentration (CMC) of the surfactant. For testing at higher or lower pH conditions, 0.1 M buffer solutions were used. Citric acid buffer was used to stabilize pH 3 while sodium bicarbonate was used for a pH 10 buffer.

FIG. 1 illustrates examples of critical micelle concentration of a composition prepared according to Example 1, termed R1 in the figure. FIG. 1 also illustrates examples of critical micelle concentration of a composition prepared according to Formula (II) formula shown below, termed R2 in the figure.

Figure 2:
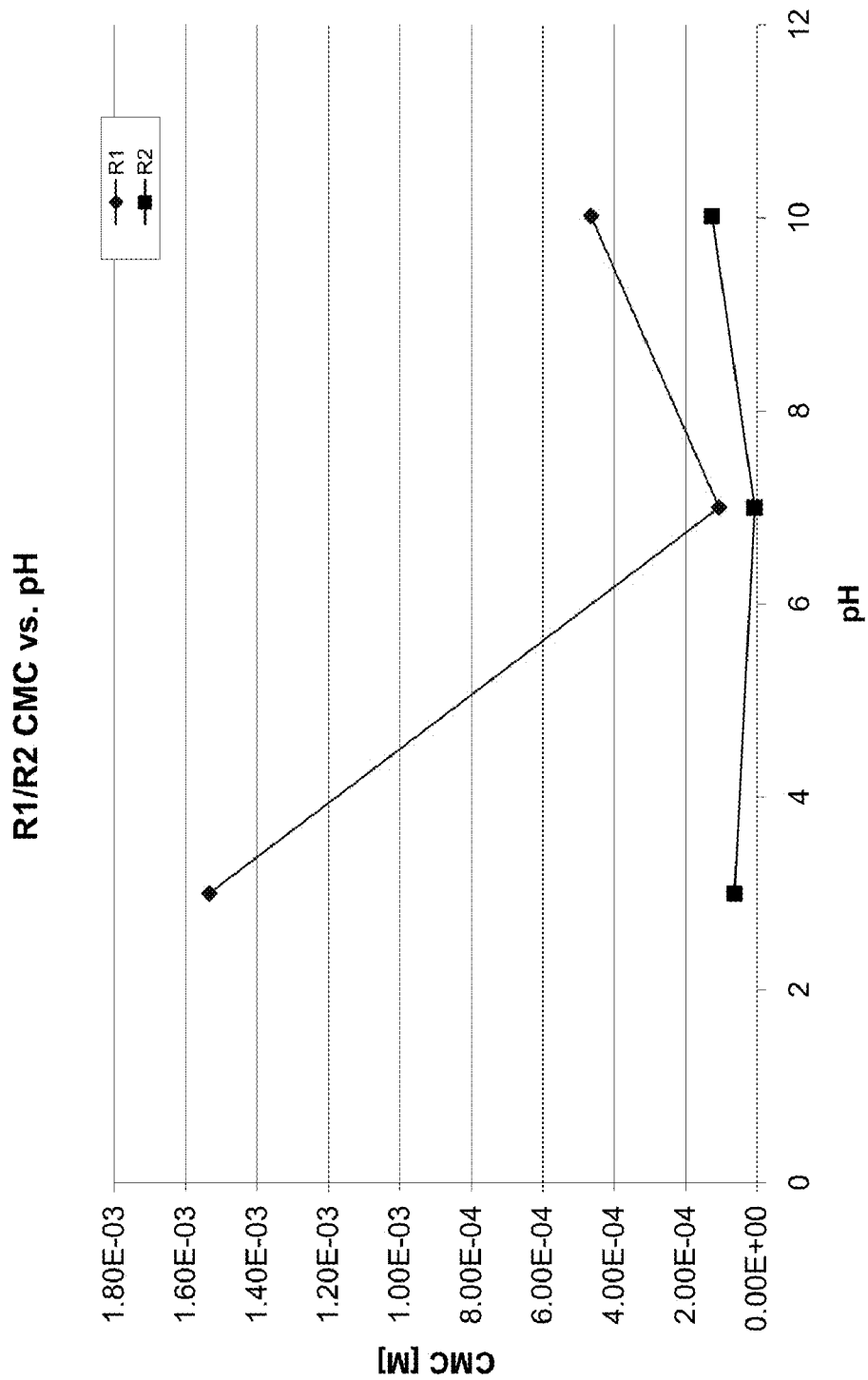
FIG. 2 shows a plot of CMC as a function of pH for two compositions, a 1:1 composition of m-resorcinol and alkylated succinic anhydride (Eka SA 210 brand alkylated succinic anhydride) and a 1:2 composition of m-resorcinol and alkylated succinic anhydride (described in more detail in the Examples).

FIG. 2 shows a plot of CMC as a function of pH for two compositions prepared according to Examples 1 and 2 (R1 and R2, respectively).

Example 6

Emulsion Stability for Oil Flow Behavior

Figure 3:
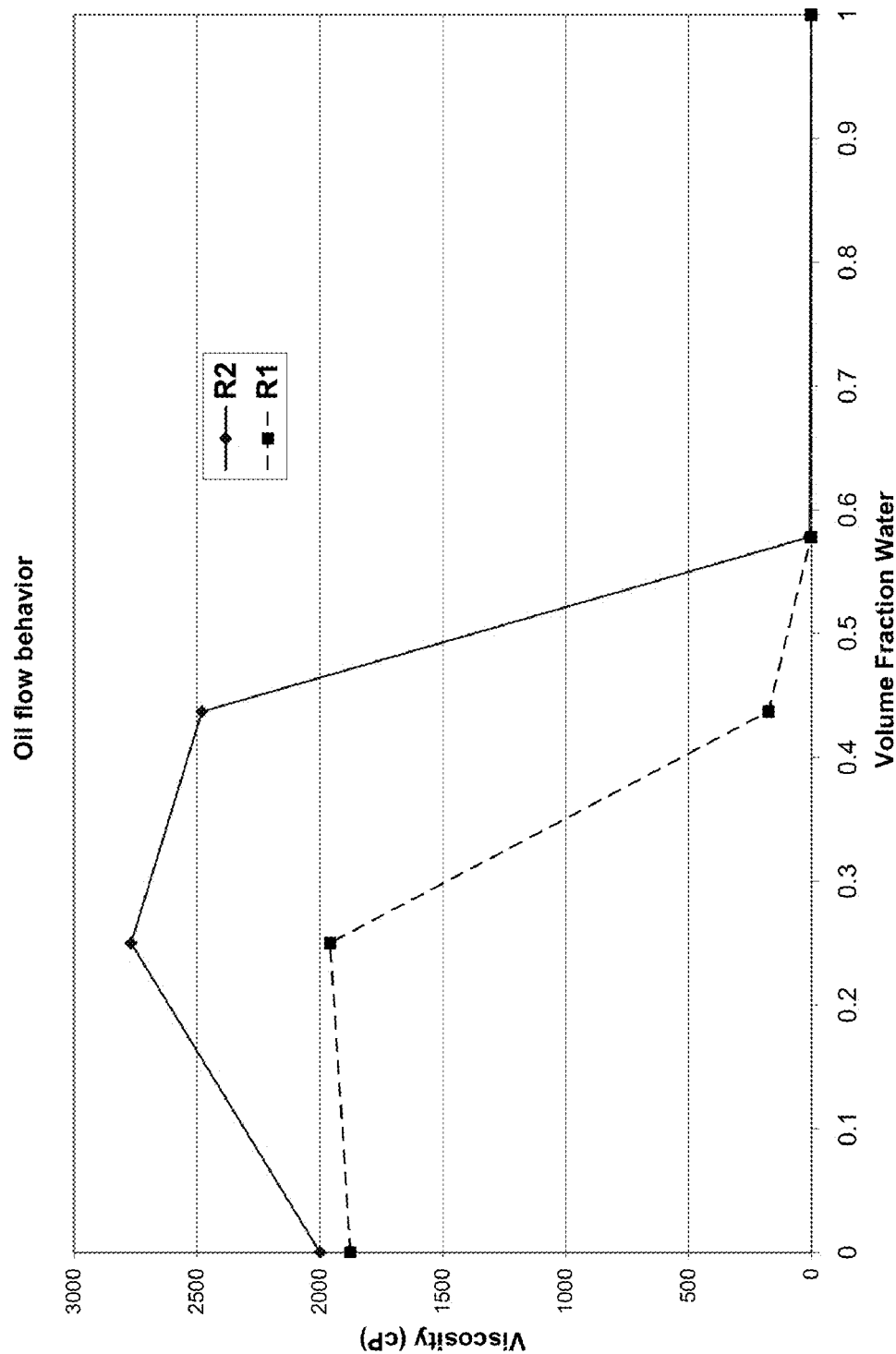
FIG. 3 compares the capabilities of the surfactant compositions (1:1 composition of m-resorcinol and alkylated succinic anhydride (Eka SA 210 brand alkylated succinic anhydride) and a 1:2 composition of m-resorcinol and alkylated succinic anhydride) in emulsifying and transporting heavy crude oils, measuring the viscosity of diluted bitumen.

In order to test the capabilities of the surfactants in emulsifying and transporting heavy crude oils, the viscosity was measured with various additions of surfactant solution on a Brookfield viscometer at 22° C. The compositions prepared according to Examples 1 and 2, were tested. Using a LV3 type spindle at 40 RPM, the diluted bitumen (residual toluene mixed with bitumen) demonstrated a viscosity of approximately 2000 cP. This diluted bitumen was then mixed with multiple ratios of a 1 wt % of the compositions in deionized water with the pH adjusted to 9 for emulsion activity. FIG. 3 illustrates the results of these tests, showing the viscosity of diluted bitumen as a function of surfactant solution addition.

FIG. 3 demonstrates that incorporation of an aqueous solution of surfactant can dramatically decrease the viscosity of diluted bitumen. As shown in FIG. 3, the addition of more than 50 vol % of a dilute aqueous solution of the compositions described herein decreases the bitumen viscosity by nearly one thousand times. The energy savings of such a system are significant, but the concomitant increase in flowrate enables much higher throughput and residence time in a pipeline.

Example 7

Reaction Between Alkenylsuccinic Anhydride and Benzyl Alcohol

A reactor was charged with benzyl alcohol (4.821 g, 44.58 mmol) and nonenyl succinic anhydride (10 g, 44.58 mmol). The mixture was stirred for about 2.5 hours at 130° C. under nitrogen. The product was then analyzed by IR spectrometry using an AVATAR 360 FT-IT spectrometer ("IR"). The sample was run in the "Attenuated Total Reflectance mode" placing the liquid sample over a Germanium crystal, which showed almost complete disappearance of the anhydride carbonyl peaks (1859 and 1778 cm-1) (i.e., only small traces of the peaks were visible) and the appearance of the ester and acid carbonyl bands (1735 and 1700 cm-1 respectively). The scheme below illustrates this synthesis:

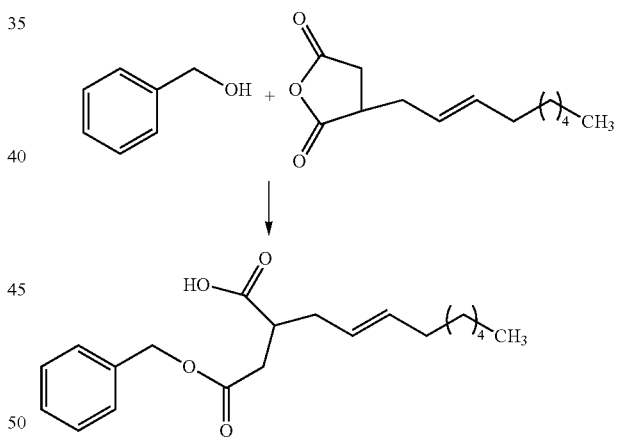

Example 8

Reaction Between Alkenylsuccinic Anhydride and Benzyl Alcohol

A reactor was charged with benzyl alcohol (3.063 g, 28.36 mmol) and Eka SA 210 brand alkylated succinic anhydride (10 g, 28.36 mmol). The mixture was stirred for about 4 hours at 130° C. under nitrogen. The product was then analyzed by IR, which showed almost complete disappearance of the anhydride carbonyl peaks (1863 and 1778 cm-1) and the appearance of the ester and acid carbonyl bands (1735 and 1704 cm-1 respectively). The scheme below illustrates this synthesis:

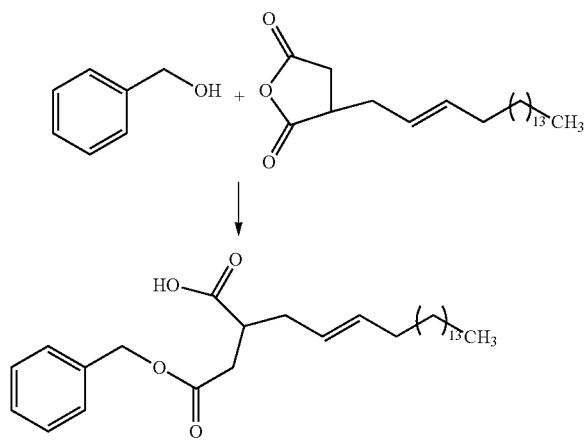

Example 9

Reaction Between a Phenol and an Alkenylsuccinic Anhydride

A reactor was charged with phenol (2.098 g, 22.3 mmol), noneyl succinic anhydride (5 g, 22.3 mmol), p-toluene sulfonic acid (1.92 g, 11.15 mmol) and 35 ml of toluene. The reactor was fitted with a Dean-Stark trap and the reaction mixture was stirred for about 5 hours under reflux. Then the reaction was washed with water (2×25 ml) to wash the p-toluene sulfonic acid and unreacted phenol, and the solvent was stripped off under vacuum in a rotary evaporator. The product was analyzed by IR, which showed almost complete disappearance of the anhydride carbonyl peaks (1859 and 1778 cm-1) and the appearance of a possible phenyl ester peak at 1758 cm-1. The scheme below illustrates this synthesis:

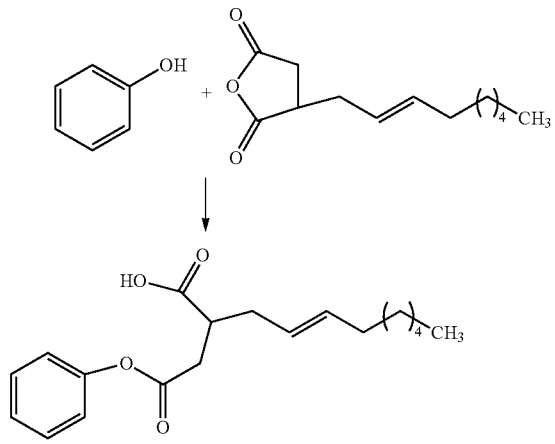

Example 10

Reaction Between a Substituted Phenol and an Alkenylsuccinic Anhydride

A reactor was charged with 2,4-dimethylphenol (1.366 g, 11.2 mmol), noneyl succinic anhydride (2.24 g, 10 mmol), p-toluene sulfonic acid (1 g, 5.8 mmol) and 35 ml of toluene. The reactor was fitted with a Dean-Stark trap and the reaction mixture was stirred for about 5 hours under reflux. Then the reaction was washed with water (2×25 ml) to wash the p-toluene sulfonic acid and unreacted phenol and the solvent was stripped off under vacuum in a rotary evaporator. The product was then analyzed by IR, which showed almost complete disappearance of the anhydride carbonyl peaks (1859 and 1778 cm-1) and the appearance of a possible phenyl ester peak at 1754 cm-1. The scheme below illustrates this synthesis:

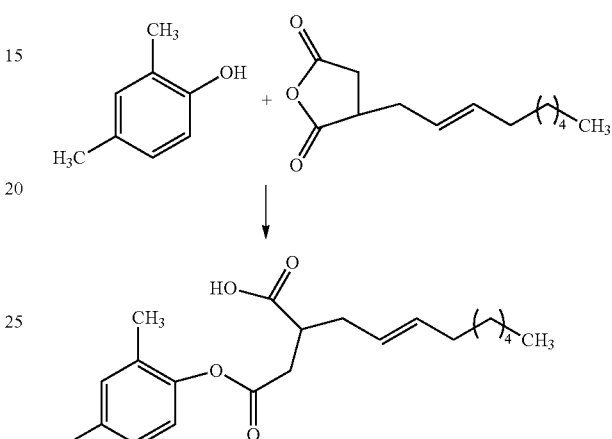

Example 11

Reaction Between an Alkenylsuccinic Anhydride and Benzyl Amine

A reactor was charged with benzyl amine (2.388 g, 22.3 mmol), noneyl succinic anhydride (5 g, 22.3 mmol) and 15 ml of THF. The mixture was stirred for about 1 hour at room temperature, and then the solvent was stripped off under vacuum in a rotary evaporator. The product was then analyzed by IR, which showed almost complete disappearance of the anhydride carbonyl peaks (1859 and 1778 cm-1) and the appearance of the amide and acid carbonyl bands (1645 and 1548 for amide I and II respectively, and 1723 cm-1 for associated acid). The scheme below illustrates this synthesis:

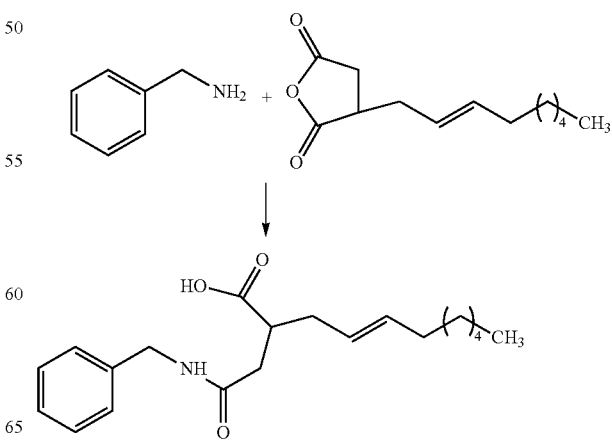

Example 12

Reaction Between an Alkenylsuccinic Anhydride and M-phenylene Diamine

A reactor was charged with m-phenylene diamine (1.534 g, 14.2 mmol), Eka SA 210 brand alkylated succinic anhydride (10 g, 28.4 mmol) and 20 ml of THF. The mixture was stirred for about 1.5 hours at RT. Then the solvent was stripped off under vacuum in a rotary evaporator. The product was then analyzed by IR, which showed almost complete disappearance of the anhydride carbonyl peaks (1863 and 1782 cm-1) and the appearance of the amide and acid carbonyl bands (1548 for amide II and a broad peak with maximum at 1703 cm-1). The appearance of these peaks may be explained by an overlapping of the amide I and acid peaks. The scheme below illustrates this synthesis:

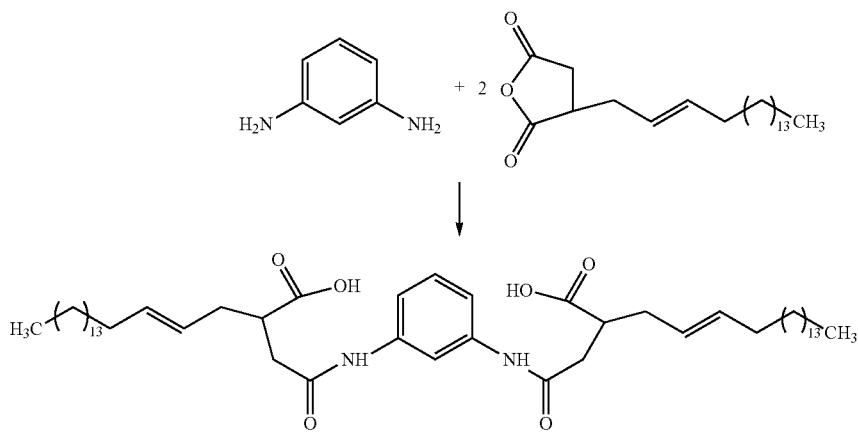

Example 13

Interfacial Tension (IFT) Measurements of Surfactants

Solutions of different aromatic based surfactants, described in Table 1 below, were dissolved in aqueous solution at 1% by weight. Deionized water was used as the control. Each aromatic-based surfactant was formulated in accordance with the corresponding Example as listed in Table 1. The pH of each solution was adjusted to 9 by the addition of 1 M sodium hydroxide. Using a KSV Sigma 702 tensiometer, the interfacial tension was measured for each solution at the interface with air, toluene and Exxon ISOPAR M fluid. Values are reported in Table 1.

TABLE 1

Table 1: Interfacial tension measurements for 1% surfactant solutions at the interface of air, toluene and ISOPAR

| | Compound | Example | IFT w/air [mN/m] | IFT w/ Toluene [mN/m] | IFT w/ ISOPAR [mN/m] |
|---|---|---|---|---|---|
| 1 | Deionized Water | Control | 71.88 | 33.12 | 72.38 |
| 2 | Heated mixture of m-resorcinol and octadecen-1-yl succinic anhydride | 2 | 26.36 | <0.01 | <0.01 |
| 3 | 2-(octadecen-1-yl)succinic acid monobenzyl ester | 8 | 28.14 | 3.73 | 8.76 |
| 4 | 2-(nonen-1-yl)succinic acid monobenzyl ester | 7 | 32.93 | 3.13 | 3.03 |

Example 14

Interfacial Tension (IFT) Measurements of Surfactants

The interfacial tension with air was measured for decreasing aqueous concentrations of a surfactant composition prepared in accordance with Example 2, starting at 1.0% by weight, 0.50% by weight and 0.10% by weight. Additionally, an unheated blend of m-resorcinol and octadecen-1-yl succinic anhydride was dissolved at the same concentrations for each compound as was used in Example 1 for comparison. Two commercially available surfactants were also tested: Tergitol 15-S-7 and Igepal CO-890. Table 2 presents the results of the IFT measurements with air for each of the tested compounds at the three different concentrations.

TABLE 2

| | Solution (by weight) | | |
|---|---|---|---|
| Surfactant Name | 1.00% IFT w/air [mN/m] | 0.50% IFT w/air [mN/m] | 0.10% IFT w/air [mN/m] |
| Heated mixture of m-resorcinol and octadecen-1-yl succinic anhydride | 26.36 | 27.07 | 27.92 |
| Unheated mixture of m-resorcinol and octadecen-1-yl succinic anhydride | 26.45 | 27.76 | 29.16 |
| Tergitol 15-S-7 | 28.03 | 28.22 | 28.11 |
| Igepal CO-890 | 44.66 | 44.63 | 44.38 |

Example 15

Surfactant Properties

Figure 4:
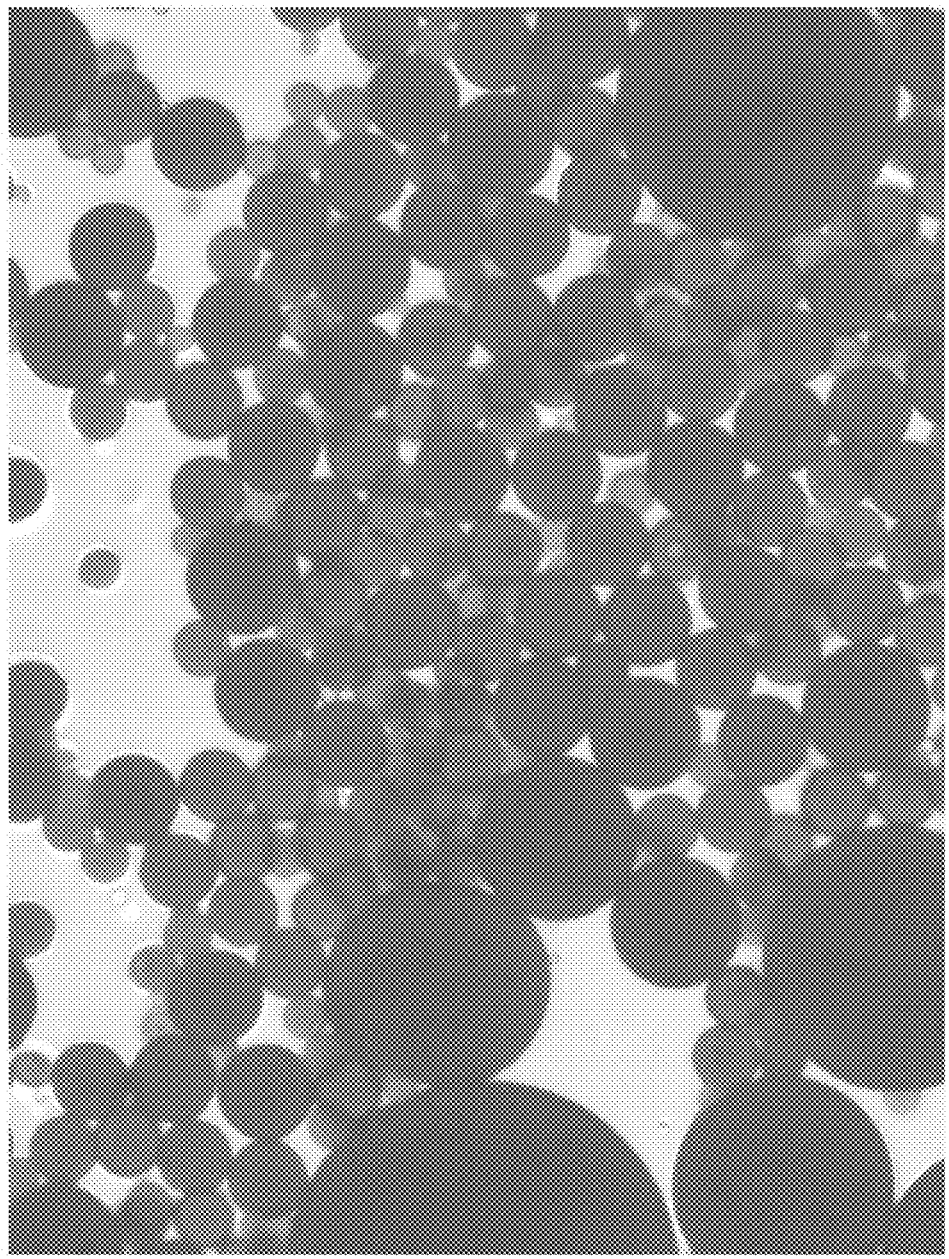
FIG. 4 shows a magnified image of oil droplets.

A sample of a compound prepared in accordance with Example 7 was dissolved in aqueous solution at 1% by weight and the pH of the solution was adjusted to 9 by addition of 1 molar sodium hydroxide. 2 mL of heavy oil (API gravity index=15.0 degrees) was mixed at 50:50 volume ratio with the surfactant solution. The mixture was shaken lightly and left to sit for 1 hour to determine the time stability of the emulsion. After about 1 hour, approximately 0.5 mL of water had phase separated in the bottom of the vial. The same phase separation was observed after 2 days of leaving the sample at rest. A magnified image of the oil droplets formed in emulsion is presented in FIG. 4, showing emulsion of heavy oil (API 15) at 50× magnification using the surfactant of Example 7. During observation, some coalescence of droplets was observed, however, the stability of the emulsion was evident over multiple days.

Example 16

Surfactant Properties

Figure 5:
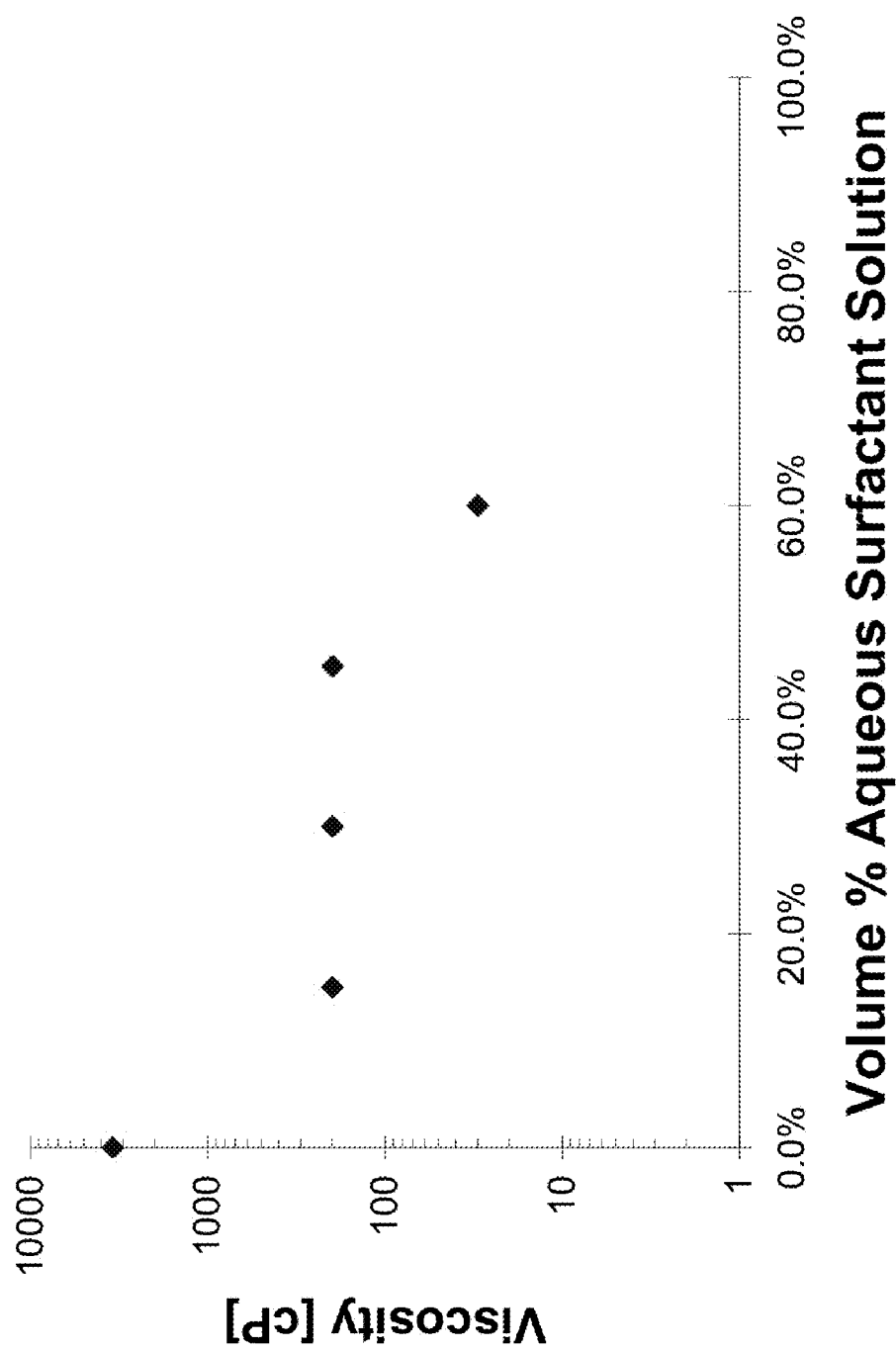
FIG. 5 is a graph showing emulsion viscosity as a function of percentage (%) surfactant solution content.

A 1% by weight sample of the compound prepared in accordance with Example 7 was prepared in aqueous solution and pH adjusted to 9 by the addition of 1 M sodium hydroxide, to form a surfactant solution. Heavy oil (API gravity index 15.0) was combined with the surfactant solution at varying water ratios to form the emulsion. Each sample was then tested in a Brookfield DVIII+Rheometer for viscosity. FIG. 5 depicts the viscosity of the resulting emulsion for a given water ratio. With use of the surfactant, a large drop in viscosity of the heavy oil is observed, even for lower water ratios. An additional drop in viscosity was noted when the volume % of water exceeded 50%.

Example 17

Reaction Between a Phenylene Diamine and Hydrophobic and Hydrophilic Glycidyl Ether A reactor was charged with m-phenylene diamine (2 g, 18.5 mmol), ERISYS GE-7 brand monoglycidyl ether of a naturally occurring C8-C10 aliphatic alcohol (3.44 g, 18.5 mmol), and 15 ml of THF. The mixture was stirred for 2 hours under reflux. Then a solution of polyethylene glycol diglycidyl ether (9.731 g, 18.5 mmol) in 10 ml of THF was added and the reflux continued for additional 4 hours. Then the solvent was stripped off under vacuum. The product was tested qualitatively to assess certain properties. First, the product was dissolved in water to show that it is water-soluble. Second, the water solution of the product was agitated vigorously, and a foam was formed, suggesting its hydrophilic and hydrophobic nature. It is envisioned that the product of this reaction will have an aromatic ring in the middle and 2 polymeric "legs" depending from it, a hydrophilic (polyethylene glycol) and a hydrophobic (alkyl chain) chain. The scheme below illustrates this synthesis:

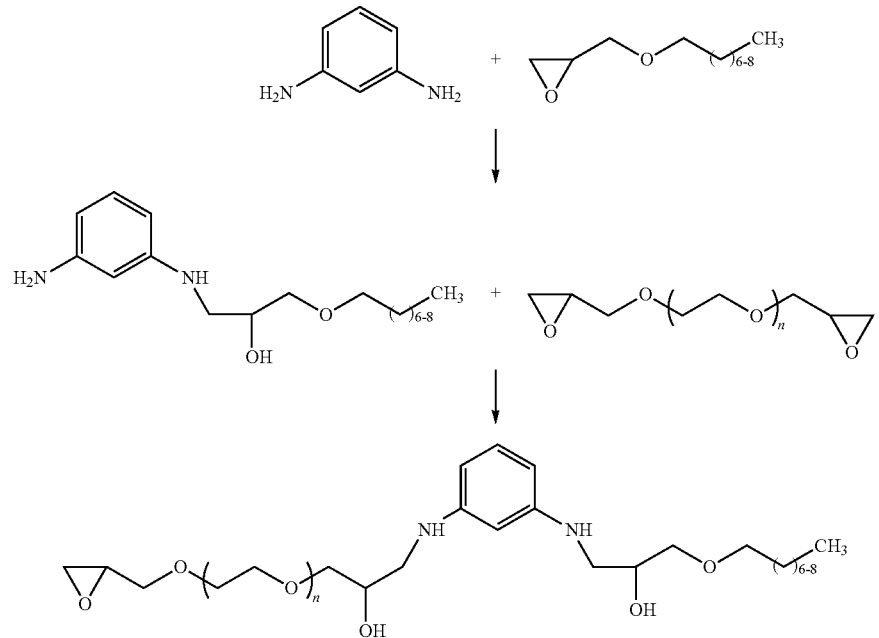

Example 18

Oily Sand Treatment 30 grams of washed sand (50/70 mesh) was mixed with 3 grams of light crude oil (API gravity index=28) by stirring until the oil was evenly distributed over the surface of the sand. For this experiment, the surfactant composition prepared in accordance with Example 2 (Surfactant A) was tested. 150 mL of a 1% surfactant solution (Surfactant A) was mixed with the oily sand by sealing in a jar and shaking by hand at a moderate pace for 5 minutes. The contents of the jar were left to sit for 1 hour and then the liquid layer was decanted from the sand. The jar was placed in an oven under vacuum at 100° C. for 3 hours, then cooled to room temperature. A sample of the dried sand was weighed and placed in a muffle furnace at 650° C. for 3 hours, then reweighed to determine the total remaining weight of hydrocarbon on the sand surface. Table 3 summarizes the effect of the surfactant solutions.

TABLE 3

| Solution used to wash oily-sand | % Oil remaining in oily-sand after wash | % Oil Recovery by Solution |
|---|---|---|
| None | 8.83% | |
| Deionized water | 7.90% | 10.54% |
| 1% Surfactant A | 0.86% | 90.24% |

EQUIVALENTS

While specific embodiments of the subject invention have been discussed, the above specification is illustrative and not restrictive. Many variations of the invention will become apparent to those skilled in the art upon review of this specification. Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth herein are approximations that can vary depending upon the desired properties sought to be obtained by the present invention.

While this invention has been particularly shown and described with references to preferred embodiments thereof, it will be understood by those skilled in the art that various changes in form and details may be made therein without departing from the scope of the invention encompassed by the appended claims.

What is claimed:

1. A composition comprising an aromatic compound and a substituted succinic anhydride, wherein
the aromatic compound has the Formula VIII:

Ar-[$G_4$]$_p$; and the substituted succinic anhydride has the Formula IX:

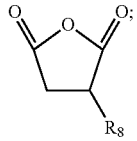

wherein Ar is selected from the group consisting of aryl, arylalkyl and heteroaryl, each optionally substituted;

each $G_4$ is independently selected from the group consisting of $OR_2$, $SR_2$, $N(R_2)_2$, $COOR_2$, $OCOR_2$, $COR_2$, $CON(R_2)_2$ and $N(R_2)_2CO$;

each $R_2$ is independently selected from the group consisting of H and lower alkyl;

$R_8$ is a saturated or unsaturated hydrophobic aliphatic group selected from the group consisting of C5-C20 alkyl, C5-C20 alkenyl, and C5-C20 alkadienyl; and p is 1 or 2.

2. The composition of claim 1, wherein p is 2.

3. The composition of claim 1, wherein the hydrophobic aliphatic group is selected from the group consisting of C8-C20 alkyl, C8-C20 alkenyl and C8-C20 alkadienyl.

4. The composition of claim 2, wherein Ar is optionally substituted phenyl or optionally substituted benzyl.

5. The composition of claim 4, wherein $G_4$ is selected from the $OR_2$ or $N(R_2)_2$.

6. The composition of claim 5, wherein $G_4$ is $OR_2$, wherein $R_2$ is H.

7. The composition of claim 6, wherein p is 2.

8. The composition of claim 7, wherein the aromatic compound is resorcinol.

9. A composition comprising an aromatic compound and a substituted succinic anhydride, wherein
the aromatic compound is resorcinol; and
the substituted succinic anhydride has the Formula IX

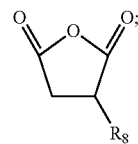

wherein $R_8$ is a saturated or unsaturated hydrophobic aliphatic group selected from the group consisting of C5-C20 alkyl, C5-C20 alkenyl, and C5-C20 alkadienyl.

10. The composition of claim 9, wherein the aromatic compound is m-resorcinol

* * * * *